United States Patent
Haddad et al.

(10) Patent No.: US 11,501,856 B2
(45) Date of Patent: Nov. 15, 2022

(54) PERSONALISED NUTRIENT DOSING WITH ON-GOING FEEDBACK LOOP

(71) Applicant: Baze Labs LLC, Green Bay, WI (US)

(72) Inventors: Isam Haddad, Berlin (DE); Philipp Wilhelm Schulte, Zürich (CH)

(73) Assignee: Baze Labs LLC, Green Bay, WI (US)

( * ) Notice: Subject to any disclaimer, the term of this patent is extended or adjusted under 35 U.S.C. 154(b) by 781 days.

(21) Appl. No.: 16/309,489

(22) PCT Filed: May 24, 2017

(86) PCT No.: PCT/EP2017/062547
§ 371 (c)(1),
(2) Date: Dec. 13, 2018

(87) PCT Pub. No.: WO2017/215893
PCT Pub. Date: Dec. 21, 2017

(65) Prior Publication Data
US 2019/0145988 A1    May 16, 2019

(30) Foreign Application Priority Data
Jun. 14, 2016   (EP) ..................................... 16174387

(51) Int. Cl.
| G16H 10/40 | (2018.01) |
| G16H 20/60 | (2018.01) |
| G16B 5/00 | (2019.01) |
| G16B 40/00 | (2019.01) |
| A61K 31/07 | (2006.01) |
| G01N 33/82 | (2006.01) |
| A23L 33/15 | (2016.01) |

(52) U.S. Cl.
CPC ............. *G16H 10/40* (2018.01); *A61K 31/07* (2013.01); *G01N 33/82* (2013.01); *G16B 5/00* (2019.02); *G16B 40/00* (2019.02); *G16H 20/60* (2018.01); *A23L 33/15* (2016.08)

(58) Field of Classification Search
None
See application file for complete search history.

(56) References Cited

U.S. PATENT DOCUMENTS

| 5,954,640 | A | 9/1999 | Szabo |
| 8,762,167 | B2 | 6/2014 | Blander et al. |
| 9,011,153 | B2 | 4/2015 | Bennett et al. |
| 2009/0006127 | A1 | 1/2009 | Bahar |
| 2010/0113892 | A1 | 5/2010 | Kaput et al. |
| 2011/0054928 | A1 | 3/2011 | Sullivan |
| 2012/0041778 | A1 | 2/2012 | Kraft |
| 2012/0083669 | A1 | 4/2012 | Abujbara |
| 2012/0130732 | A1 | 5/2012 | Blander et al. |
| 2015/0338387 | A1* | 11/2015 | Ehrenkranz ............ A61K 31/12 436/501 |
| 2016/0055758 | A1 | 2/2016 | Francis |

FOREIGN PATENT DOCUMENTS

| CA | 2 756 465 A | 4/2013 |
| DE | 10 2004 040 308 A1 | 3/2006 |
| EP | 1 248 213 A1 | 10/2002 |
| GR | 20120100381 A | 2/2014 |
| JP | 2002-41669 A | 2/2002 |
| WO | 2006/060445 A2 | 6/2006 |
| WO | 2006060445 A2 | 6/2006 |
| WO | 2014/087252 A2 | 6/2014 |
| WO | 2015176994 A1 | 11/2015 |

OTHER PUBLICATIONS

MacGregor, James T., et al. "Spontaneous' genetic damage in man: evaluation of interindividual variability, relationship among markers of damage, and influence of nutritional status." Mutation Research/Fundamental and Molecular Mechanisms of Mutagenesis 377.1 (1997): 125-135.*
International Search Report for PCT/EP2017/062547 dated Oct. 9, 2017 [PCT/ISA/210].
Johnson et al, "RID Control. New Identification and Design Methods", Sprinqer, 2005, pp. viii-543 (559 Pages total).
Rezzi, S. et al:"Metabonomic approaches to nutrient metabolism and future molecular nutrition." Trends in Analytical Chemistry, vol. 52, 2013, pp. 112-119 (8 Pages Total).
Watzke. H. J. et al.. "Personalizing Foods", in: Moskovitz, H. et al ES (Eds), An integrated approach to new food product development, CRC Press, 2010 pp. 113-173, (45 pages total).

* cited by examiner

*Primary Examiner* — G Steven Vanni
(74) *Attorney, Agent, or Firm* — Sughrue Mion, PLLC (57) ABSTRACT

A method for providing nutritional supplement information for a subject is proposed, including a sequence of steps in given order and repeated at least once after a time span of at least 2 days or one week for adapting the provided nutritional information:
A) taking a sample from the subject;
B) analyzing said sample to determine the nutritional status;
C) based on the results calculation of nutritional supplements to improve the nutritional status;
D) providing individualized nutritional supplement information.
This sequence involves the prediction of at least one initial characteristics matrix and multiplication of this matrix weighted with factors, with an initial recommendation vector for the calculation of a target profile vector after a given first time interval from the profile vector as determined in step B), and in each following cycle adaptation by adapting at least one of the characteristics matrix and the weighting factors.

24 Claims, 3 Drawing Sheets

PERSONALISED NUTRIENT DOSING WITH ON-GOING FEEDBACK LOOP

CROSS REFERENCE TO RELATED APPLICATIONS

This application is a National Stage of International Application No. PCT/EP2017/062547, filed on May 24, 2017, which claims priority from European Patent Application No. 16174387.7, filed on Jun. 14, 2016, the contents of which are incorporated by reference.

TECHNICAL FIELD

The present invention relates to the technical field of human or animal nutrition, nutritional advice and nutrient supplements (also known as dietary or nutritional supplements). More particularly, the present invention is in the technical field of adapting nutrient supplements to an individual's specific nutrient needs by running an on-going feedback loop consisting of regular blood tests, other data input, accordingly dosed nutrient supplements and user intake.

PRIOR ART

Long-term general performance as well as short and medium-term performance of an individual are influenced fundamentally by nutritional supply. While humans are quite resistant to imbalances in nutritional supply maximum performance and long-term performance can only be assured if the nutritional supply is well-balanced and meets the individual's nutritional needs. These nutritional needs are influenced by many factors, including age, activity profile, sex, health condition, climate, etc.

Optimization of the nutritional supply of individuals so as to allow for optimum performance and is not only the object of general advice from food specialists but is also the object of various patents.

JP-A-2002041669 addresses the problem to effectively provide information indispensable for the purpose of efficiently managing the situation of a user desiring health management, sickness improvement and diet and to permit the user to easily and precisely manage adopting food and a foodstuff amount at every meal. An environment is proposed where a food DB managing food, the constitution foodstuff names and the foodstuff amounts can easily be retrieved via the Internet and food and foodstuff adopting amounts are registered and managed for an arbitrary period and supplied to the user. The target foodstuff amounts of the respective foodstuffs are set for the respective users. Effective information corresponding to the adopting situation such as food for supplementing the excessive/lacked foodstuffs, a means for improving sickness and exercise information for realizing target weight can easily be obtained from a result acquired.

DE-A-102004040308 proposes and claims a method for automatic, individual advice on nutrition and eating routines involving storing person-related nutritional data in an electronic, magnetic or optical nutrition data bank, determining the person-related nutritional food characteristics by preparing a number of nutritional characteristics in an electronic, magnetic, optical etc. data bank for individual food-stuffs and/or kinds of foods, followed by identifying the food-stuffs on the basis of an identification device. The nutritional characteristics are assigned to the food-stuffs by an identification unit by comparison of the identified food-stuffs with the food-stuffs and/or types of food filed in the data bank. Processing of the nutritional data follows, with recommended data output.

US-A-2009006127 proposes a method of providing nutritional guidance to people suffering from one or more medical conditions. The invention provides a method of ranking different nutrients according to their beneficial or harmful properties to a particular medical condition. The method can further take into account a multitude of different medical conditions and produce lists of good and bad nutrients by taking account of each medical condition separately and then combining the results to produce a master list of good vs. bad foods or nutrients for the person suffering from more than one medical condition.

WO-A-2014087252 proposes a system and a method to provide health-related information. A user interface on a computing device may provide assessment information associated with an assessment of a user's health. Further, sensed information associated with at least one of biological information, physiological information and physical activity of the user can be received from a different device which is configured to sense information. Moreover, a processing subsystem that includes a processor and processor-readable media can be configured, to process the sensed information, to provide processed user information, and to determine health-related information, via the processing subsystem, using the assessment information and the processed user information. Furthermore, the processed user information and the health-related information can be transmitted via a communication subsystem, to the computing device, and the health-related information, can be provided at the computing device via the user interface substantially contemporaneously with the reception of the sensed information.

CA-A-2756465 relates to a method and system that converts nutritional and ingredient information from labels following the scanning of the item's bar code or related symbologies and from other sources into an easy to understand standardized set of measurements that are illustrated and displayed using graphics and simple text. The information provided is further supported by virtual and live coaching programs, supplemental information, self-monitoring and communication tools to help individuals, families and groups.

U.S. Pat. No. 8,762,167, and similarly U.S. Pat. No. 90,111,563, proposes a system for the generation of personalized, health and performance programs for individuals based on various biomarkers and performance and lifestyle assessments. In one embodiment, a single diagnostic test of blood or other biological specimen(s) is used to determine key biological marker levels. Information and assessments of the user's physical performance, life style and health and wellness goals is also collected and provided to an expert system that matches the biomarker levels and assessments to a knowledgebase of scientific knowledge about biomarker levels and health and fitness outcomes. Personal recommendations and advice on nutrition and exercise is then generated based on questions to be answered by the user, which may be used to help individuals reach their diet, fitness, and wellness goals and improve their physical and mental performance and well being in measurable ways.

WO-A-2006060445 discloses nutritional supplements and methods for formulating and customizing such nutritional supplements. Also disclosed are methods for formulating and customizing nutritional supplements to subject deficiencies for preventing disease and protecting against nutritional losses and deficiencies.

US-A-2010113892 relates generally to providing nutrigenomic information tailored to that of the customer so that the customer can make informed decisions regarding diet, exercise, risks of disease and other health issues that result in a healthier lifestyle and prolonged lifespan. In particular it provides systems for research and commercial purposes, particularly for research for improving dietary constituents, personalized nutrition and diets, and of nutrient-gene interactions involved in diseases. The invention further relates to a method for doing business encompassing establishing and running a nutrigenomic research super-market and providing validated nutrient intake data to health care practitioners.

US-A-2011054928 proposes a personalized nutritional supplement method that includes the steps of affiliation; training; client assessment; review; recommendations; order placement; and order fulfillment. A personalized nutritional supplement method that includes blood testing is also provided.

US-A-2012130732 proposes a personalized, health and performance program generated for individuals based on various biomarkers and performance and lifestyle assessments. In one embodiment, a diagnostic test of blood or other biological specimen(s) is used to determine key biological marker levels. Information and assessments of the user's physical performance, life style and health and wellness goals is also collected and provided to an expert system that matches the biomarker levels and assessments to a knowledgebase of scientific knowledge about biomarker levels and health and fitness outcomes. Personal recommendations and advice on nutrition and exercise is then generated, which may be used to help individuals reach their diet, fitness, and wellness goals and improve their physical and mental performance and well-being in measurable ways.

EP-A-1248213 proposes a health advising method by which a person who wants to ask an advice about the person's health can prepare information necessary to ask an advice at any time and the adviser can offer an effective advice to a large number of people. An adviser receives a request of a user for an advice about the user's health and then sends a life inquiry sheet, a blood preservation kit, and a blood sample collection needle to the user by mail. Upon receiving the life inquiry sheet on which user has written the answers, the kit containing the blood sample of the user, and the blood sample collecting needle, the adviser examines the blood sample in the kit and inputs the results of the examination and the answers to the inquiry into a pathology analysis expert system, which makes an advice to the user on the basis of the inputted data and the knowledge stored in a database. The adviser reports the advice thus made to the user.

US-A-2016055758 describes a method for delivering to a user a biometric display containing a graphic representation of the user that communicates health related information about the user. The method includes steps of receiving via a communication network information associated with physical characteristics of the user and health related information associated with the user and generating a biometric display of the user based on the received physical characteristics associated with the user. The biometric display represents a virtual persona of the user tailored toward the received physical characteristics associated with the user. The method also includes steps of generating health parameters based on the received health related information associated with the user and associating the health parameters with their respective body parts on the biometric display. The health parameters communicate to the user health related information regarding their respective body part on the biometric display. The method also includes a step of delivering to the user via the communication network the biometric display along with the associative health parameters.

SUMMARY OF THE INVENTION

Humans are unique in their molecular set-up, lifestyle and environment. According to the proposed approach subjects are provided with either recommendations, products or both, that are personalized to their unique profile to enable an optimal fitness and wellness.

Specifically, the proposed integrated platform uses—amongst other inputs—blood testing as meaningful and actionable molecular data source and establishes an on-going feedback loop of repeated tests, either personalized recommendations, products or both and user actions.

This on-going stream of data—including the molecular response triggered by either certain recommendations, products or both—and the resulting learnings are characteristic of this platform. The learning algorithms described in further detail below enable the on-going improvement and personalization of both recommendations and products over time. This dynamic evolution of recommendations, products or both over time based on previous learnings is the core and novel element of this invention. In comparison, prior art is only static over time, i.e. recommendations, products or both are not changed based on previous learnings based on multidimensional numerical calculations.

One concrete product at hand is dietary supplements whose nutrient composition is personalized via the proposed platform. At the same time, the scope of the invention goes beyond this particular use case and incorporates more data input sources and categories as well as use cases both in humans as in animals.

More specifically, the present invention relates to a method for providing nutritional supplements (nutritional supplement advice) for a subject, said method including a sequence of the following steps in given order:

A) taking a sample from the subject, wherein the sample can be at least one of blood, blood serum, blood plasma;

B) analyzing said sample to determine the nutritional status of the subject;

C) based on the results of step B) calculation of the required advice and/or nutritional supplements to improve the nutritional status of the subject (the improvement not being limited to this, also included indirectly are e.g. fitness, wellbeing);

D) providing individualized nutritional supplement advice and/or individualized nutritional supplements to the subject.

The sequence of A)-D) is repeated after a time span of at least two days, or at least 4 days or at least 7 days, for adapting the provided nutritional advice and/or nutritional supplements in step D) of the second sequence based on the development of the subject in the time interval between the sequences.

When talking about a time span of e.g. at least 2 days or at least one week, this time span is to be calculated between the moments of taking a blood sample.

In practice and preferably the method is carried out in a multidimensional numerical manner involving numerical optimization algorithms and matrix calculations, in particular as follows:

the first initial cycle step C) involves the prediction of at least one initial absorption characteristics matrix ($A_k$, $B_{p(k)}$, . . . can be a linear combination of a personalized component $A_k$ and at least one peer group component $B_{p(k)}$, and the multiplication of this least one initial absorption characteristics matrix ($A_k$, $B_{p(k)}$, ...), weighted with weighting factors ($\alpha$, $\beta$, ... in the sense of a linear combination with as many weighting factors as characteristics matrix components), with an initial recommendation vector ($d_1$, basically a vector, each component of which represents the daily dose of the corresponding nutritional supplement component) for the calculation of a target profile vector ($x_1^\dagger$, basically a vector, each component of which represents the target value of the corresponding component in the blood) after a given first nutritionally supplemented time interval from the profile vector ($x_0$, basically a vector, each component of which represents the analytical results of the corresponding component in the blood) as determined in step B).

Typically the first step involves the determination of a target profile vector ($x_1^\dagger$) based on knowledge about appropriate levels for the respective individual and the recommendation vector ($d_1$) is calculated by using an inverse of the initial absorption characteristics matrix.

In each or at least the majority of each following cycles, adaptation is implemented in that the difference between the previously calculated target profile vector ($x_n^\dagger$) and the profile vector ($x_n$) as determined in the actual analysis step B) is minimized by adapting and thereby personalizing at least one of the initial absorption characteristics matrix ($A_k$, $B_{p(k)}$, ...) and the weighting factors ($\alpha$, $\beta$, ...), and using the adapted absorption characteristics matrix ($A_k$, $B_{p(k)}$, ...) and weighting factors ($\alpha$, $\beta$, ...) for the calculation of the required next recommendation vector ($d_{n+1}$) and for the prediction of the next target profile vector ($x_{n+1}^\dagger$) after a given next nutritionally supplemented time interval.

The dimensionality of the recommendation vector and the target profile vector is preferably at least 2, preferably at least 3 or 4, and e.g. in the range of 5-15.

Using this scheme an optimum nutritional supplementation is possible without risk of overshooting in particular in the initial stages of the process, and allows for and as fast as possible steady state establishment, i.e. and as fast as possible determination of a recommendation vector which is stable, and except for changes of the individual, hardly needs to be changed anymore.

This feedback loop is a key element of the entire approach: It increases the value for the user over the time he uses the product, through the ongoing personalization of nutrient supplementation by adapting it dosing formula according to the success of its previous dosing formulas. This means that similar to a series of experiments, the delta between actual and target nutrient state is minimized as the dosing formula in an increasingly better manner reflects the individual biochemistry of a given user. Its novelty compared to prior art is explicitly in the dynamic nature of this numerical multidimensional adaption process, i.e. in the fact that the dosing formula changes overtime and includes a number of components, normally at least 2, preferably at least 3 or at least 4 or 5 individual components are analyzed in the blood and influenced by the targeted nutritional supplements. A detailed example based in simulated data is given further below.

According to a first preferred embodiment the nutritional supplements are selected from at least one of the following group: vitamins, vitaminoids, minerals, herbals, botanicals, amino acids, enzymes, carbohydrate, fiber, fatty acids, proteins, peptides, terpene-based biological molecules, including carotenoids, steroid-based biological molecules, including hormones, pyrrol-based biological molecules, including tetrapyrrols, alkaloid-based biological molecules, including caffeine, prebiotics, probiotics, flavonoids, antioxidants.

Step A) preferably involves the taking of a sample by the subject, applying the sample to a solid substrate, preferably provided with sample stabilization agents, and immobilizing and drying the sample on said substrate to form a dried sample. All these steps can be carried out at home or at another place, which is not a point-of-care and the steps do not necessitate the help of medically trained personnel.

Preferably said step A) further involves sending said sample by mail to a place for carrying out step B).

Said solid substrate or any other kind of sample carrier can further preferably be provided with identification information, preferably in computer readable form, including barcode, QR code, OCR readable text. This identification information can already be specific to the subject, it can however also simply be an identification information characteristic for the (blood) sample carrier device. Establishing of the link between the sample carrier and the subject undergoing the process can also be carried out for example by reading the identification information with the smart phone of the subject and interacting with a background digital platform associating the corresponding individualized blood sample carrier to the subject.

For step C) preferably further input information of the subject is taken account of, in particular at least one of the following individual information: sex, age, ethnic affinity, physical activity, mental activity, general status, nutritional information, climatic information, lifestyle information, but also molecular and genomic or genetic information.

For a second or further sequence preferably yet further input information of the subject of the time interval between the sequence and the corresponding actual sequence is taken account of for step C), in particular at least one of the following information: use of the supplied nutritional advice and/or nutritional supplement, physical activity, mental activity, general status, general nutritional information, climatic information, lifestyle information.

The sequences can be carried out at regular intervals over an extended time span of typically at least 1 week, or 3 months, preferably of at least 6 months, or in some cases at least a year. The sequences can be carried out at least every 2 days or at least every week, preferably at least every second or third week, further preferably every month. After for example a time span of 3 months or 6 months, time span for establishing a settled status of the subject, this frequency can be continued but preferably the frequency is reduced after having reached a steady-state situation.

The frequency of carrying out the sequences can also further preferably be determined by and based on the results of the analysis in B) and the calculation in C) and wherein the step D) includes information provided to the subject (1) when the next (blood) sample needs to be taken. As a matter of fact, by monitoring the development of the nutritional status of the subject it is possible to derive whether the subject needs frequent adaptation of the nutritional scheme or not. Therefore the calculation in step C) can be adapted to optimize the sample taking process and to reduce it to the minimum necessary and to the amount as required.

Step C) can preferably include a step of manufacturing individualized nutritional supplements based on the required nutritional supplements for the subject and step D) includes sending of these individualized nutritional supplements, preferably together with instructions how to consume, to the subject. These individualized nutritional supplements can either be produced as a specific formulation (tablet, sachet or the like) including the required combination of nutritional supplements, or it can be produced as a kit of parts including the required elements and instructions to the user how to combine the specific elements. It is even possible to produce a daily adapted formulation scheme, so that for each specific day a specific tablet/sachet is provided. This scheme can be advantageous in a situation where a smooth increase or decrease of the supply of a particular supplement is necessary to avoid overshooting or overdosage effects.

Step B) may further preferably include the step of mass spectrometric analysis of the blood, preferably further including a step of chromatographic separation or ICP, in particular for the determination of minerals and/or protein markers characterizing the nutritional status of the subject, in particular characterizing the required needs for at least one of: vitamins, vitaminoids, minerals, herbals, botanicals, amino acids, enzymes, carbohydrate, fiber, fatty acids, proteins, peptides, terpene-based biological molecules, including carotenoids, steroid-based biological molecules, including hormones, pyrrol-based biological molecules, including tetrapyrrols, alkaloid-based biological molecules, including caffeine, prebiotics, probiotics, flavonoids, antioxidants.

Characteristic data specific to the subject (1), in particular analysis data of the respective blood sample and further input data of the subject (1), can be stored for each sequence of steps A)-D) in a database, and can be used at least for the calculation in step C) and wherein the calculation in step C) includes taking account of the development of the characteristic data over time.

According to yet another preferred embodiment, in step D) the individualized nutritional supplement advice includes the daily-recommended doses of nutrients, which are to be taken up additionally.

The calculation in step C) can further preferably take account of maximal or minimal recommended possible doses of the individual supplements and preferably further can take account of ranges for the nutrient profile to smoothly shift the actual nutrient profile towards the optimal range.

The present invention furthermore relates to a computer program product, in particular to be used on a mobile device such as a smart phone, for use in a method as described above, in particular to carry out at least one of the following steps: to return the measurement values of step B) and/or the results of step C) and/or the individualized nutritional supplement information to the subject, displaying the corresponding information, allowing the subject to input personal information, allowing the subject to automatically, using a camera of the corresponding device, read identification information on a device for taking up the blood sample, and/or track the activity of the subject automatically to provide for information as defined in claim 6 for the interval between sequences.

In addition, the present invention relates to an individualized nutritional supplement as determined and produced according to a method as defined above.

Last but not least the present invention relates to a kit of parts for carrying out the method as described above comprising at least a blood sample carrier, preferably provided with identification information and/or specific areas marked for depositing at least one blood droplet, as well as at least one of the following items: puncture device; transfer device; alcohol wipes; plaster; gauze swab; user manual; specimen bag including a sachet with desiccant; identity code, barcode or QR code, identifying the particular kit; preaddressed envelope suitable and adapted for the sample carrier; further components that are required by regulation in a given country.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
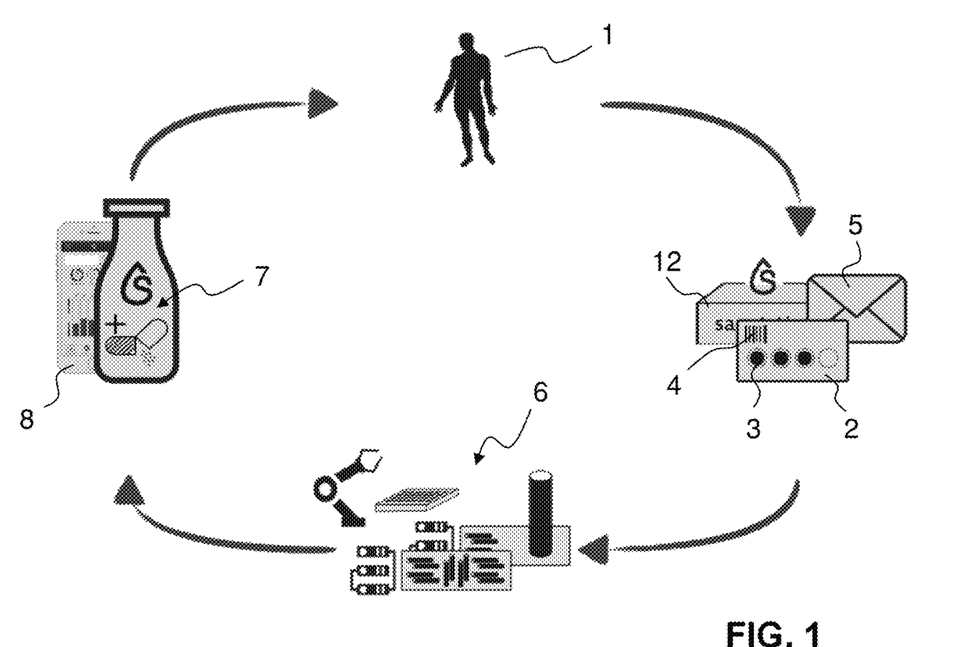
FIG. 1 shows a schematic general flow scheme of the proposed approach of an integrated platform and ongoing optimisation cycle.

FIG. 1 provides an overview of the key components of the proposed approach/platform. A convenient sample kit 12 for home use provides the user 1 with a tool to provide a blood sample 2 for laboratory analysis. The dried blood sample card 2 preferably comprises specific areas 3 for applying and drying droplets of blood thereon, and further the sample card includes identification information 4 which can be user specific but which can also be, in order to keep anonymity, just be characteristic for the card, the link between the user 1 and the corresponding analysis data determined from the sample card 2 only being established downstream in the process. High-throughput laboratory methods in a corresponding analysis and data processing facility 6 form a robust and low-cost diagnostic platform to analyse the molecular composition of the blood sample 3. The analytical results are captured in the digital biobank and interpreted by the recommendation algorithms of the platform intelligence. The output is communicated to the user e.g. via a smart phone 8 through an understandable user interface and actionable recommendations are provided. Dietary supplements 7 with personalised nutrient contents are produced and delivered to the subject 1. Users either act on the recommendations, take the supplements with varying degrees of compliance or do both. Afterwards, the described cycle starts anew.

The impact of the user actions on the molecular composition of his blood describes a user-characteristic feedback. Based on this feedback a user-specific model is generated, comprising the user's demands and resorption characteristics. Through each cycle, this model is updated and rendered more precise via algorithmic approaches.

Any of the three components sample (kit), laboratory analysis and actionable product/information are necessary to fuel and push the recommendation cycle. However, the sample kit for home testing can be as well replaced by a kit which is applied by medically trained persons, the laboratory analysis can be replaced by a point-of-care testing device, the personalised product can be some kind of actionable recommendation, which improves individual fitness and wellness.

The individual elements are characterized as follows:

Sample Kit

The sample kit enables the user to conveniently sample blood himself, normally at home or another place which does not have to be a point-of-care and does not involve medical personnel. So sampling takes place without the need of being medically trained or a third person who is.

The blood sampling using a dried blood sample fulfils three criteria:

It is safe and easy to use. From the moment of unpacking throughout the different steps its use is clear and intuitive, and in addition to that the corresponding technology is well-established and approved.

It allows sampling a defined and reproducible sample of blood.

The blood sample is stabilized after drying, such that it can be sent with a conventional postal service and without the need of cooling. The change in concentration of analytes of interest in the sample does not exceed validated ranges over the course of days without cooling. The general analysability in as far as the present method for nutritional advice/supplement is not affected within this timespan.

The two main parts of the kit 12 are a puncture device, i.e. a device that does the actual puncture to collect blood; and the sample carrier 2, i.e. the device that stabilizes the blood sample 3 and makes it easily transportable.

Puncture Device:

Within the scope of this approach, blood means preferably specifically capillary whole blood. Accordingly, a puncture device is typically a single-use lancet or a lancet pen in combination with disposable lancets. Additionally, a novel class of devices can be considered which emerged through recent developments, which puncture the skin through micro- or nano-tubes while drawing capillary blood through a vacuum into the device.

A typical syringe used for venepuncture is possible as well.

Sample Carriers:

The collected blood is stabilized and sent to the laboratory in the form of dried whole blood. Possible carriers 3 for the dried blood 3 are either filter papers in arbitrary formats, typically as dried blood spot cards, or dried blood spot sticks. Possible products are available from sources such as Tasso Inc under the trade name HemoLink, TAP devices as available by Seventh Sense Biosystems, or micro sampling device is available from Neotyrex.

To stabilize the blood by drying is optional but preferred. Accordingly, other sample carriers are possible as well, including capillary tubes, the typical blood collection tubes, as well as those puncture devices, which draw the blood into a reservoir before releasing it.

Stabilization of the blood can be promoted by agents, which are contained by or coated on the sample carriers 2. Typically they affect coagulation, oxidation or other chemical, physical or biological effects, which destabilise the concentration, accessibility or general analysability of the target analytes in the blood over time.

Depending on the sample carrier, a transfer device can be advisable or makes the process convenient and more reproducible. It allows transferring a defined volume of drawn or collected blood from the puncture device onto or into the sample carrier. This can be for example a precision or non-precision pipette. Capillaries or capillary arrangements which collect and distribute the sampled blood are also covered by this definition.

Content of the Kit:

The kit preferably contains at least one of the following items: Puncture device; Sample carrier 2; Transfer device (if applicable); Alcohol wipes; Plaster; Gauze swab; User manual; Specimen bag including a sachet with desiccant (if applicable); Identity code, barcode or QR code, identifying the particular kit; Preaddressed envelope suitable for the sample carrier; Any other components that are required by regulation in a given country.

Not part of the kit itself but strongly connected to the kit is a software, typically a mobile app, which lets users order, register or track the kit and through which results from the blood analysis are communicated.

Laboratory Analysis

Relevant Markers:

The blood analysis, as one central component of the proposed approach, is carried out to unravel the molecular blood profile of the tested person 1. This is typically composed of markers characterizing the following substance classes:

minerals, in particular trace quantity elements small molecules including terpene-based biological molecules, including carotenoids, steroid-based biological molecules, including hormones, pyrrol-based biological molecules, including tetrapyrrols, alkaloid-based biological molecules, including caffeine, prebiotics, probiotics, flavonoids, antioxidants amino acids carotenoids fatty acids steroids vitamins polypeptides and proteins.

The panel of markers is not necessarily limited to the described substance classes. It may also include genetic markers, RNA-based markers or a blood cell count.

The analytical methods for the detection are in most cases mass-spectrometry based and typically coupled to a preceding chromatography procedure. This has the advantage that with one analytical run, multiple markers can be measured simultaneously as long as they belong to a substance class, which is sufficiently homogenous to be detected with the same method and sufficiently heterogeneous to be uniquely distinguishable from each other.

The analytical procedure is identifying the minimal set of analytical methods, which is able to fully qualify and quantify all analytes at the same time with optimised time and cost efficiency.

Automation:

The general laboratory process comprises the following steps:

- Split the sample into as many sub samples, as different extraction protocols exist.
- Extract the analytes from the samples with appropriate extraction protocols.
- Perform chemical modifications like oxidations or derivatisations of those extracts where necessary, in order to make the analytes separable or detectable.
- Perform the instrumental analysis with the sample.
- Perform a raw data analysis of the instrumental signal data yielding the full quantities of the defined markers.

Those steps are maximally automated by lab robotics, meshing the different steps on the split samples optimally, such that a total turnover time of a single sample can be minimized and time intervals of critical steps are kept constant across samples to ensure maximal reproducibility.

Depending on the particular method different steps (e.g. extraction and derivatization) can be also directly combined in the same process step, if suitable.

While being processed through the automation, the samples are always uniquely identifiable by the identity code, which is part of the according sample kit.

Full quantification of the markers is performed by quantifications with external standard calibrations.

Technologies:

- LC-QQQ-MS: Most low molecular weight molecules and proteinogenic markers are identified by liquid chromatography coupled to a triple-quadrupole mass-spectrometer (MS). Different analytical runs are tailored towards the physical properties of the subsets of the markers, i.e. proteinogenic extracts and water-soluble and fat-soluble compounds. Qualification and quantification of the analytes is typically performed in MRM (multi-reaction-monitoring) mode in the MS.
- ICP-MS: This method is performed to identify the elemental composition of the samples, i.e. analyse the trace and quantity elements. This is typically done, after the samples underwent a stringent oxidative extraction procedure.
- GC-FID/GC-Q-MS: This method is used for low molecular weight molecules with a high volatility. It can be applied to identify and quantify fatty acids, which usually undergo an esterification to extract and analyse also the fatty acid composition of the membrane bound triglycerides.

The here described technology, however, is a means to an end to perform the molecular blood analysis. It is from a state-of-the-art perspective a very cost-effective approach to assess a large and flexibly growing set of markers from low blood volumes. As technology evolves over time and the categories of relevant markers expand, particular analytical methods could change or even be replaced by different measurement principles.

Data Analysis:

Instrumental raw data analysis is performed fully automated, including steps such as identification of the analyte spectra, integration of the chromatographic peak areas, performing the calibration of the external standards, quantifying the markers against the calibrations. Outcome of the entire analytical procedure is a table assigning to each marker the original concentration in the sample.

IT Platform

Figure 2:
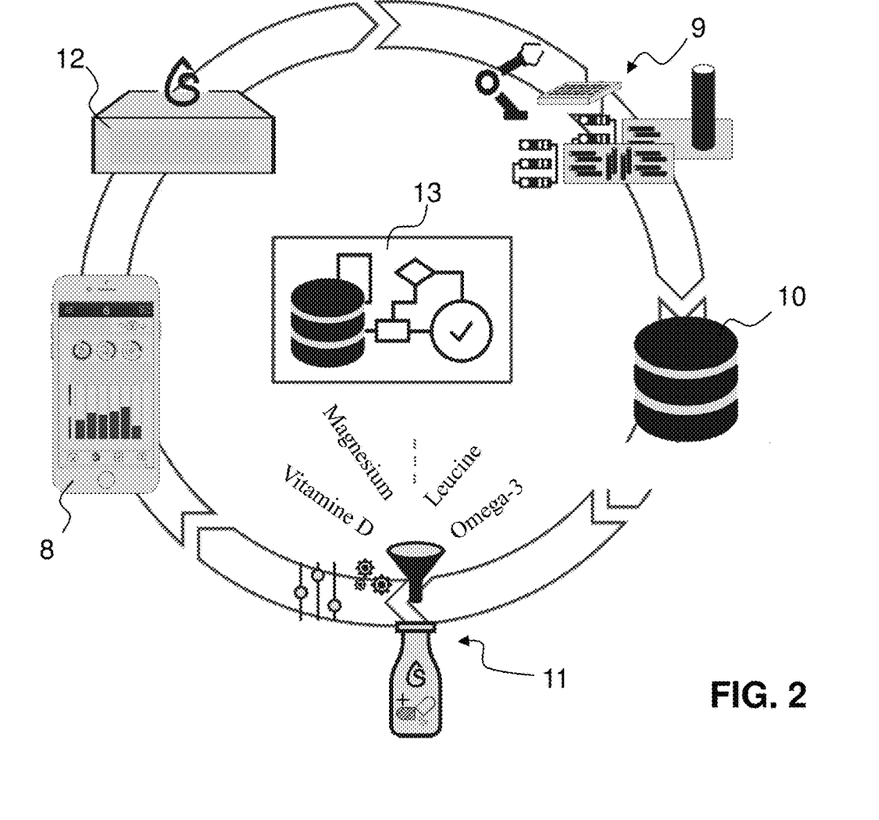
FIG. 2 shows another schematic flow scheme of the proposed approach.

Digital Round-Trip:

The journey of one sample is at any step reflected by the digital platform underlying the entire process. The corresponding digital roundtrip is illustrated in FIG. 2.

It starts with the sample kit 12 represented by its identity code. When the user 1 uses the sample kit he registers it through a mobile app and connects the kit, and accordingly his blood sample with his personal identity. However, knowledge of the kit identity code and ownership of the app are sufficient to claim the identity over time. This allows using the system in a completely anonymous fashion.

In the laboratory 9 the sample is analyzed, which is formally a digitalization of the blood sample properties. The results in terms of determined quantities are exchanged with the digital platform 13, enriching the information existing for the particular sample and user.

Based on the measured values and possibly existing profile information of the user, the recommended daily nutrient doses are calculated by algorithms in the platform intelligence 10. This subcomponent of the system implements the feedback-loop-based learning procedures and integrates the personalised user and peer-group specific nutrient demands and resorption models as explained as well further below.

The calculated doses are pushed to the production site 11, where the personalised supplements are produced.

While the user 1 is consuming his personalised supplements 7, he documents through the mobile application any events related to his general wellness or deviations from regular supplement intake protocol. This information is stored with his profile at the platform intelligence 10, to close the feedback-loop and strive for further personalisation.

API and Data Security:

The digital platform 13 communicates with the data exchanging entities throughout a RESTful API (Representational State Transfer Application Programming Interface). This API is the single and central entry point to the digital platform.

Consuming from the Eco System:

The personalization of the recommended supplement doses is based on the measured blood values. However, the feedback loop is only fully closed if additional information concerning the user's lifestyle etc. is known. The most basic information is the regularity with which the user took the recommended supplements in the interval between individual measurement sequences. In addition to this, any information related to the user's general status, fitness and nutrition is valuable and allows painting a more complete picture. Also other genetic (like particular gene sequencing data) or phenotypic information (e.g. microbiome data, just to name one) can be integrated.

As a large list of services exists which produce large amounts of this kind of data, and make them available throughout APIs, the user is free to authorize the digital platform, to integrate data managed by these services into his data records stored in the digital platform.

Producing for the Eco System:

In the same manner as other services provide data to the digital ecosystem of general status, lifestyle and nutrition tracking, the proposed service potentially allows for letting the user share his data with other services through the API.

Recommendation System

Goal of the Recommendation System:

One platform output is to give a user, who exposes unbalanced nutrient profiles, actionable recommendations that let him balance his nutrient profile in a desirably short period of time. As a consequence, the recommendation system needs to derive from the nutritional profile the daily-recommended doses of nutrients, which are to be taken up additionally or other convenient lifestyle recommendations.

The recommendations are preferably constrained by two criteria:
1. According to scientifically accepted guidelines narrow optimal ranges exist for the individual's nutrient profile. Complying with the recommendations should smoothly shift the actual nutrient profile towards the optimal range, i.e. with a measureable improvement and without overshooting effects.
2. The actual recommendations never exceed accepted maximal or minimal recommended doses.

Calculating Daily Doses:

Let r be a recommendation function and d be the nutrient recommendation profile; a vector with $d_i$ being a quantitative recommendation. This is in its simplest form a daily dose for a particular nutrient. Let's assume for the following, that d comprises only nutrient recommendations. Let x be the inner nutrient profile; a vector comprising the measured nutrient profile with concentration $x_j$ for nutrient j in whole capillary blood. Note that any nutrient i as part of the recommendation profile is not necessarily the same compound as the components j of the inner nutrient profile. For an individual k the actual recommendation profile is calculated by $$d = r_k(x, y, \alpha, A_k, \beta, B_{p(k)}, \gamma, C_k, \delta, D_{p(k)}, \omega_k)$$

$A_k$ and $B_{p(k)}$ are functions or matrices describing how the concentration of an inner nutrient component $x_j$ is effected by a particular recommendation $d_i$. $A_k$ is personalised for an individual k while $B_{p(k)}$ is personalised for k's peer group p(k). $\alpha$ and $\beta$ are coefficients which assign different weights to $A_k$ and $B_{p(k)}$ with $\alpha + \beta = 1$ and $\alpha > 0$ and $\beta > 0$.

The influence of k's external influences on his inner nutrient profile is also taken into account, by the external influence profile vector y where coefficients $y_m$ characterise particular and quantifiable external influence categories. These categories may include—without being limited to—fitness data, nutritional intakes and patterns and behaviours, as well as seasonal and regional aspects, so generally speaking climatic aspects. $C_k$ and $D_{p(k)}$ are functions or matrices describing how the concentration of an inner nutrient component $x_j$ is effected by a particular external influence characteristic $y_m$. $C_k$ is personalised for an individual k while $D_{p(k)}$ is personalised for k's peer group p(k). $\gamma$ and $\delta$ are coefficients which assign different weights to $C_k$ and $D_{p(k)}$ with $\gamma + \delta = 1$ and $\gamma > 0$ and $\delta > 0$. If y is a function over time between two measurements, d may also vary over the same time period.

Finally, $\omega_k$ describes the optimal inner nutrient concentration profile of an individual k according to scientifically accepted guidelines. k's inner nutrient profile is considered to be in balance if the following equation holds:

$$\omega_k - x = 0$$

It is noteworthy that none of $A_k$, $B_{p(k)}$, $C_k$ and $D_{p(k)}$ as functions of x or y fulfill necessarily the criteria of additivity or homogeneity; i.e. they do not necessarily describe linear systems in terms of the systems theoretical reception of linearity. This reflects that two different recommended nutrient dosages $d_v$ and $d_w$ can have a different individual influence on an inner nutrient component $x_j$ as in the combination of both. As an example: The efficiency of the supplementation of Calcium, largely depends on the inner concentration of Vitamin D3.

The concept of the here described nutrient recommendation function r is easily extendable and will be extended over time to another recommendation function q which derives in the same manner recommendations e to influence the inner nutrient concentration profile x through external factors, as fitness or lifestyle.

$$e = q_k(x, y, \alpha_e, A_k, \beta_e, B_{p(k)}, \gamma_e, C_k, \delta_e, D_{p(k)}, \omega_k)$$

Ultimately the concept can be extended such that r and q can be combined with the goal to give combined recommendations in the domains of nutrient supplementations and lifestyle advice to balance the inner nutrient profile:

$$(d, e) = r_k \otimes q_k$$

The described approach is tailored towards balancing the inner nutrient concentration profile by deriving recommendations for nutrient supplementation, external factors and the combination of both. Finally, this concept is easily extendable to other objectives in the fields of nutrition, fitness, wellness by defining an appropriate objective function $\omega_k - x = 0$ and defining according functions for $A_k$, $B_{p(k)}$, $C_k$ and $D_{p(k)}$ (and others if necessary).

Frequency of Testing:

The frequency of measuring the inner nutrient profile is determined by the recommendation system itself. The effect of a recommendation d on an inner nutrient profile x is statistically predicted. If the confidence bands of the prediction for a given confidence level $\varphi$ at a future point in time gets too broad, the inner nutrient profile needs to be re-measured. At this time point a new test is pro-actively recommended by the system.

The statistical confidence of the prediction depends mainly on three factors:
1. The on-going degree of personalisation: The less personalised (i.e. the smaller $\alpha$) the broader are the confidence bands.
2. Time elapsed since the last test: The longer, the less certain the forecast becomes.
3. Changes in the lifestyle, health, wellness, fitness or regional parameters: Changes in intrinsic and extrinsic effects on the physiology of an individual can lead to unpredicted effects on the nutrient demand and consequently profile.

Feedback Loop:

As already mentioned the feedback loop is one essential component of the entire approach: It increases the value for the user over the time he uses the product, through the ongoing personalization of nutrient supplementation by adapting it dosing formula according to the success of its previous dosing formulas. This means that similar to a series of experiments, the delta between actual and target nutrient state is minimized as the dosing formula increasingly better approximates the individual biochemistry of a given user. Its novelty compared to prior art is explicitly in the dynamic nature of this adaption process, i.e. in the fact that the dosing formula changes overtime. A detailed example based in simulated data is given on page 17.

The fundamental assumption is, that every human needs different intake dosages of nutrients daily, but also has different resorption characteristics, making different and tailored recommendations necessary. Determination of the particular resorption characteristics is one challenge, which is tackled by the approach at hand. In the following explanation only the very reduced model $$d = r_k^*(x, \alpha, A_k, \beta, B_{p(k)}, \omega_k)$$

is considered. It is easy to show that the presented principle is also applicable to the generalised mode $r_k$ as well as to $q_k$ and $r_k \otimes q_k$.

The first time the user uses the product, almost nothing is known of his resorption characteristics. But phenotypic information like gender, age or ethnic affinity allow to group the user k in a particular peer group p(k). Accordingly, a $B_{p(k)}$ exists which is most suitable for the user. Based on the first measured inner nutrient concentration profile $x_0$ a recommendation $d_1$ can be given.

For the first application of the model at t=0 it is $\alpha=0.5$ and $\beta=0.5$ (although not being limited to this start configuration) with $A_k = B_{p(k)}$. For the next scheduled test at t=1 the outcome of $x_1$ is predicted and noted as $x_1^\dagger$. The results of the next test are compared with the prediction and from the deviation $x_1^\dagger - x_1$ an updated version $A'_k$ is derived, such that the dosing $d_1$ derived from $d_1 = r_k^*(x_0, \alpha=1, A'_k, \beta=0, B_{p(k)}, \omega_k)$ would have led to a prediction $x_1^\dagger = x_1$. The updated version of $A'_k$ is used for the recommendation at t=2. At the same time $\alpha = 1-\beta$ increases by a portion which depends on the relative difference of $x_1^\dagger - x_1$. This mechanism is the adaptive learning step, which ensures that the resulting recommendations converge smoothly towards a stable personalization.

Accordingly, $A_k$ is derived from $B_{p(k)}$ and constantly becomes more precise the more cycle iterations a user undergoes. This is reflected by an increasing weight $\alpha$ and decreasing weight $\beta$.

A second benefit is a constant improvement of $B_{p(k)}$ on the peer group level. The more the content of the digital biobank grows, the more associations of phenotypic peer group information to constantly refined resorption characteristics $A_k$ exists. This allows to diversify the set of $B_{p(k)}$'s according to the peer group information and assign from the beginning a better matching and faster improving model to new users from t=0.

Finally, the entire approach allows to not only model and personalise the resorption characteristics ($A_k$), the influence of external factors ($C_k$) and subsequently refine the according peer group data ($B_{p(k)}$ and $D_{p(k)}$). Over time, and with a sufficient degree of personalization it even allows to match the user's subjective input, reflecting immediately his fitness, wellness, against his inner nutrient profile and accordingly perform an adaptive learning process on the optimal inner nutrient profile $\omega_k$ with the goal to even personalize this component of the model.

An Example:

The described feedback mechanism is now rendered as a specific example. For this purpose the following simplifications are made without any loss of generality:

External influences $C_k$ or $D_{p(k)}$ are not considered.

Recommendations e for external factors are not considered. Consequentially, combined recommendations (d, e) $\forall e \neq 0$ are not considered.

The functional relation of the recommendation profile d on the inner nutrient status x is approximated by linearization. This means in particular that the change of the inner nutrient status, does not depend on the status itself.

A depletion of inner nutrient levels is not explicitly taken into account.

Cross interactions of nutrients are not considered, i.e. every recommended nutrient effects exactly one inner nutrient.

The following example is given for two inner nutrients: The 25-OH-Vitamin $D_3$ (Calcifediol) level and the Omega-3 fatty acid level.

Those nutrients can be affected by the direct supplementation of Calcifediol and Eicosapentanoic acid (EPA)/Docosahexanoic acid (DHA):

For Calcifediol a blood (serum) level between (50-125) nmol/L is considered to be normal, while a level in the range of (70-100) nmol/L is considered to be optimal. Typical daily doses of supplemented Calcifediol are in the range between 60 mmol and 300 mmol (and can even vary largely from this range).

For the Omega-3 status a blood level of (4-12) % EPA+DHA of the total fatty acid content is considered as normal, while (8-11) % are considered to be optimal. These nutrients are typically supplemented as fish oil capsules, whereas the typical ratio of DHA:EPA is 2:3. Usual recommendations for supplementation are in the range of (1-3) g EPA+DHA.

We assume now, that for an individual $k \in p(k)$ at t=0 the following inner nutrient profile was assessed:

$$x_0 \begin{pmatrix} \text{Calcifediol} \\ \text{Omega-3} \end{pmatrix} = \begin{pmatrix} 30 \text{ nM} \\ 3\% \end{pmatrix}$$

Based on this, the user is receiving a recommendation profile:

$$d \begin{pmatrix} \text{Calcifediol [mmol]} \\ \text{EPA [g]} \\ \text{DHA [g]} \end{pmatrix}.$$

Furthermore, we assume for this particular user the following absorption characteristics:

$$A_k = B_{p(k)} = \begin{pmatrix} 5 & 0 & 0 \\ 0 & 0.05 & 0.05 \end{pmatrix} \cdot \begin{pmatrix} \text{nM/mmol} & 0 \\ 0 & \%/g \end{pmatrix}.$$

Accordingly, the inner nutrient profile is expected to reach the state $x_{t+1}$ after a single instance of compliance with the recommendation profile:

$$x_{t+1} = x_t + (\alpha \cdot A_k + \beta \cdot B_{p(k)}) \cdot d$$

$$x_{t+1} = x_t + R_1 \cdot d$$

For the first cycle of adaption the recommendation profile d is to be found which would lift after 20 iterations the inner nutrient profile to $$x_{1,20}^\dagger = \begin{pmatrix} 60 \text{ nM} \\ 5\% \end{pmatrix}.$$

In its general form the recommendation function would be reduced to $$r_k: d_1 = \frac{1}{n} \cdot R_1^{-r}(x_{t+n} - x_t)$$

Were $R_1^{-r}$ denotes the right inverse of $R_1$. We find (for $\alpha=\beta=0.5$) under the constraint that typically the ratio of EPA:DHA in dietary supplements is 3:2, that $$R_1^{-r} = A_k = B_{p(k)} = \begin{pmatrix} 0.2 \text{ mmol/nM} & 0 \\ 0 & 12 \text{ g/\%} \\ 0 & 8 \text{ g/\%} \end{pmatrix}$$

and finally $$d_1 = \begin{pmatrix} 0.3 \text{ mmol} \\ 1.2 \text{ g} \\ 0.8 \text{ g} \end{pmatrix}.$$

Figure 4:
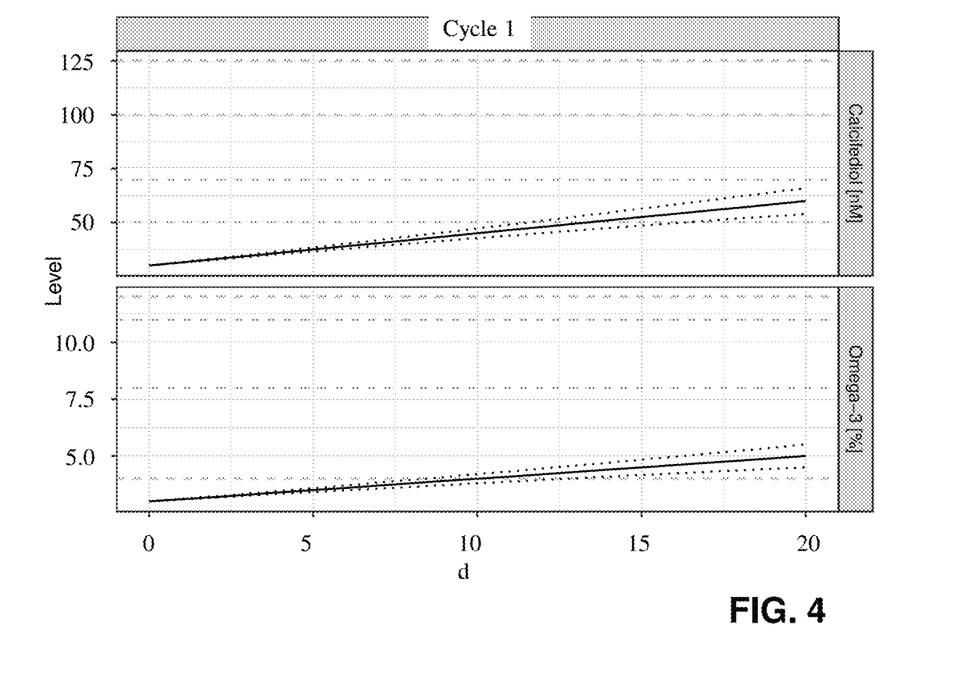
FIG. 4 shows the simulated progress of an inner nutrient profile x of an individual k after 20 days of daily intake of a recommended dose "d=(0.3 mmol Calcifediol, 1.2 g EPA, 0.8 g DHA)"; the light grey stripe indicates the normal range of the according nutrient, the dark grey stripe the optimal range; the upper and lower bounds of the simulation's confidence band are depicted as the dotted line, assuming an increase of ±0.5%/day.

The simulation of $x_t$ over 20 iterations (days) of the recommended intake is depicted in FIG. 4. The uncertainty of the predicted x is assumed to be $$\pm \frac{\beta}{100} = \pm 0.5\%$$

per iteration.

Accordingly a total uncertainty of 20% is reached after 20 days. At this time point a reassessment of x and a comparison with $x_{1,20}^\dagger$ should be made.

We assume now, that the reassessed data for $x_1$ (i.e. at the end of cycle 1) was found to be $$x_1 = \begin{pmatrix} 48 \text{ nM} \\ 4\% \end{pmatrix}.$$

The training coefficient $\alpha$ is then calculated by $$\alpha_1 = 1 - 0.5 \cdot \sqrt{\left(\frac{x_1^\dagger - x_1}{x_1^\dagger - x_0}\right)^2_{Calcifediol} + \left(\frac{x_1^\dagger - x_1}{x_1^\dagger - x_0}\right)^2_{Omega\text{-}3}}$$

which gives in this case $\alpha=0.68$ and accordingly $\beta=0.32$. Furthermore, the actual resorption characteristic of the first cycle was $$A_k = \begin{pmatrix} 3 & 0 & 0 \\ 0 & 0.025 & 0.025 \end{pmatrix} \cdot \begin{pmatrix} \text{nM/mmol} & 0 \\ 0 & \%/g \end{pmatrix}$$

as this one solves the equation $x_1 = x_0 + 20 \cdot A_k \cdot d_1$. Accordingly, the resorption characteristics for a second cycle is $$R_2 = (\alpha \cdot A_k + \beta \cdot B_{p(k)}) = \begin{pmatrix} 3.64 & 0 & 0 \\ 0 & 0.033 & 0.033 \end{pmatrix} \cdot \begin{pmatrix} \text{nM/mmol} & 0 \\ 0 & \%/g \end{pmatrix}.$$

Additionally, the uncertainty of the next iteration reduces to $$\pm \frac{\beta}{100} = \pm 0.32\%$$

which gives in total 31 iterations (days) until the total uncertainty of the prediction reaches 20%. This whole procedure was simulated over three cycles. All calculated parameters are found in table 1. Note that the actual reassessments $x_i$ are random, yet realistic guesses.

TABLE 1

Depicted are the main parameters of the simulation over 3 cycles. Note that according to $\alpha$ the number of iterations in cycle 3 should be 100. As it would, however, not be recommended to reassess the actual value of x_i after a longer period than a month, the number of iterations was set to 31.

| Cycle | $x_i$ | Iterations | d | $x_i^\dagger$ | $\alpha$ | $A_k$ |
|---|---|---|---|---|---|---|
| 1 | $\begin{pmatrix} 30 \text{ nM} \\ 3\% \end{pmatrix}$ | 20 | $\begin{pmatrix} 0.3 \text{ mmol} \\ 1.2 \text{ g} \\ 0.8 \text{ g} \end{pmatrix}$ | $\begin{pmatrix} 60 \text{ nM} \\ 5\% \end{pmatrix}$ | .50 | $\begin{pmatrix} 5.00 & 0 & 0 \\ 0 & 0.050 & 0.050 \end{pmatrix}$ |
| 2 | $\begin{pmatrix} 48 \text{ nM} \\ 4\% \end{pmatrix}$ | 31 | $\begin{pmatrix} 0.2 \text{ mmol} \\ 2.34 \text{ g} \\ 1.56 \text{ g} \end{pmatrix}$ | $\begin{pmatrix} 70 \text{ nM} \\ 8\% \end{pmatrix}$ | .68 | $\begin{pmatrix} 3.64 & 0 & 0 \\ 0 & 0.033 & 0.033 \end{pmatrix}$ |
| 3 | $\begin{pmatrix} 66 \text{ nM} \\ 7.6\% \end{pmatrix}$ | 31 | $\begin{pmatrix} 0.14 \text{ mmol} \\ 1.45 \text{ g} \\ 0.97 \text{ g} \end{pmatrix}$ | $\begin{pmatrix} 80 \text{ nM} \\ 10\% \end{pmatrix}$ | .90 | $\begin{pmatrix} 3.21 & 0 & 0 \\ 0 & 0.032 & 0.032 \end{pmatrix}$ |

Figure 5:
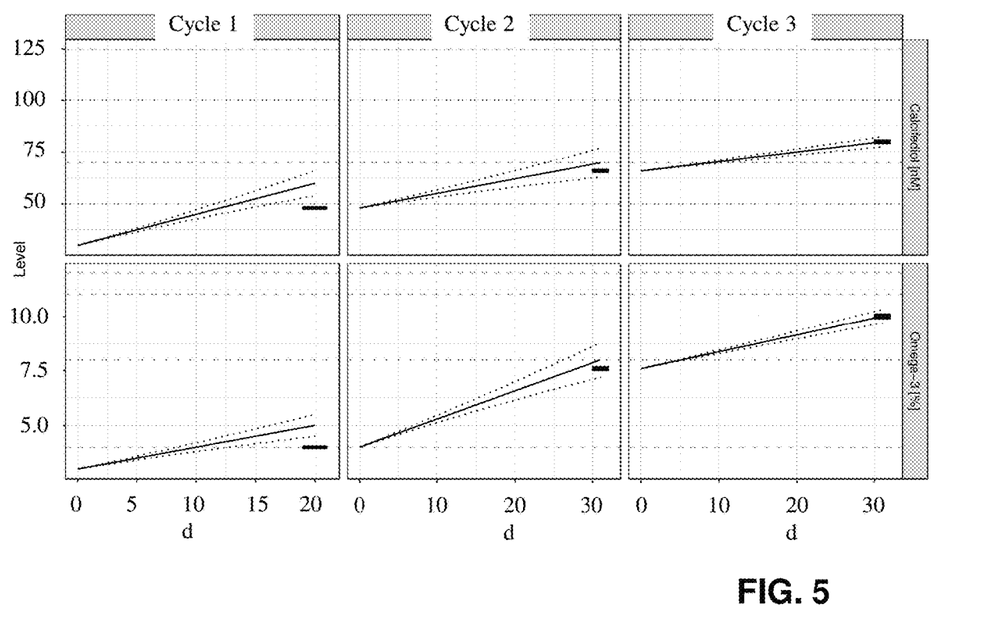
FIG. 5 shows the simulated progress of an inner nutrient profile x of an individual k over three cycles of dosage adaption; the light grey stripe indicates the normal range of the according nutrient, the dark grey stripe the optimal range; the upper and lower bounds of the simulation's confidence band are depicted as the dotted line; the black horizontal bars at the end of each cycle indicate the presumed (but random) measurements and mark the start values of the subsequent cycles.

A complete overview of the whole simulation is found in FIG. 5. From the data shown it becomes obvious, that the strategy of adaptive adjustment of the resorption characteristics $A_k$ based on the tracked feedback of the reassessments ensures a targeted repletion of deficient inner nutrient profiles.

Furthermore it is shown that this adaptive adjustment strategy is strictly personalized: Even if two individuals from the same peer-group would have started the whole process with the same nutrient profile $x_0$ and accordingly with the same dosage recommendation $d_1$ they would have been treated with different recommendations after the first cycle if they would have differed in their $x_1$.

Notion of Power Shots:

To make recommendations as convenient as possible for the user, power shots can be used. In cases where nutrients are not supplemented but are solely taken up by natural food, or a mixture of natural food and supplements, the recommended daily doses can be too abstract to understand. Hence, a power shot is a particular amount of one nutrient, or a combination of nutrients. Quantities of foods containing these nutrients can then be expressed in power shots.

The concept is similar to the German notion of a Broteinheiten, defining an amount of carbohydrates in natural food.

This concept can even be expanded, to

Power shots as equivalents to particular lifestyle actions, e.g. a walk in the sun is worth x power shots for Vitamin $D_3$ negative power shots, where a certain action, intake or event can have a negative effect on a particular nutrient profile value.

Mobile App

Functionality:

One integral part of this entire approach is a software—preferably a mobile application—which supports the entire approach and guides the user. For the remainder of the document the software is abbreviated with app.

The software has mainly five functions (see also FIG. 3):
1. As part of the digital round trip, measurement values are returned to the user from the lab through the digital platform to the app. It represents the information in different perspectives, i.e.
   Plain measurement values
   Aggregated measurement values for different outcome categories (i.e. a dashboard view, for e.g. physical fitness)
   History of former measurements, for particular markers or fitness categories.
2. The app displays the recommendations derived from the personalised modelling based on the measurement. It also lets the user track to which extent he complied with the recommendations.
3. It also enables the user to input and track other relevant daily data from the domains, of fitness, lifestyle and nutrition. Ideally the app is also integrated with other third party services.
4. The app keeps track of any data shared with or generated by the digital platform. The user is at any time in full control of his data and is able to revoke access to and from third party services and can also delete data generated by using the system.
5. Through the app the complete lifecycle of kits, samples and supplements can be tracked: Ordering the kit, registering a sample, checking a samples status, ordering supplements, ordering third party products, managing the subscription, being informed of recommendations, including the recommendation to redo a test.

Figure 3:
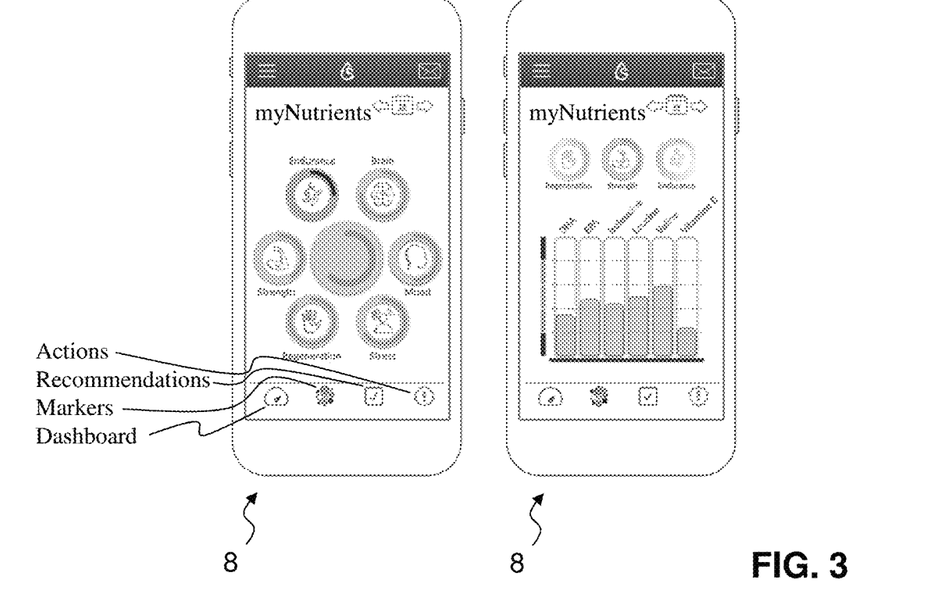
FIG. 3 shows a possible graphical representation of the results on a smart phone of a user, more specifically two sketched mockups of the app, showing plain measurement data (right) and measurement data aggregated by fitness category (left)

From this description it follows, that the app is an unobtrusive digital companion to the user. This is important, as it closes the feedback loop and drives the confidence levels for increasing personalization.

Personalised Nutrients

Set of Nutrients

To ensure beneficial impact for the users, one needs to make it as easy as possible for them to take action. One concrete product to facilitate action and drive compliance on nutrients is to provide users with dietary supplements that are personalized according to their nutrient needs as determined by our recommendation system.

The nutrients which can be supplemented include, but are not limited to, amino acids, carotenoids, fatty acids, quantity elements, trace elements and vitamins.

Personalization Process:

The nutrients are delivered to the user in concentrations that are personalized according to his nutrient needs as determined by our recommendation system. This can be both in the form of fully personalized nutrient concentrations, i.e. for n=1 ("custom-tailored"), or an appropriate combination of a given set of nutrient building blocks, i.e. for n>1 ("made-to-measure"). This can include as well the use of dietary supplements that are being produced and sold by other parties.

a combination of the latter two.

The personalization process can be done both manually as well as automatically via compounding machines. Intermediary stages are possible as well.

Possible Galenic Formulations:

To ensure beneficial impact for the users, one needs to make it as easy as possible for them to take action. This includes the convenience of taking the personalized supplements, which is to a good amount driven by the galenic formulation(s), used. These can include, but are not limited to, liquid, powder and/or compressed (tablets, including effervescent forms thereof, suppositories) versions.

Delivering Personalised Supplements:

The personalized supplements can be delivered conveniently to the users. This can be done via direct home delivery or via third parties. The packaging of the personalized supplements will be convenient and intuitive to facilitate compliant intake. For this, the daily doses will be packed into daily packs ready for convenient intake.

| LIST OF REFERENCE SIGNS |
| --- |
| 1 user/subject |
| 2 solid substrate for blood sample |
| 3 blood sample |
| 4 barcode on 2 |
| 5 envelope |
| 6 high throughput laboratory analysis and data management and nutritional information calculation facility |
| 7 individualized nutritional supplement formulation |
| 8 smart phone or other communication device |
| 9 high throughput laboratory analysis facility |
| 10 database and calculation facility |
| 11 facility for manufacturing individualized nutritional supplement formulations |
| 12 sample kit |
| 13 digital platform |

The invention claimed is:

1. A method for providing nutritional supplements for a subject, said method including a plurality of cycles comprising the following steps in given order:
   A) taking a sample of at least one of blood, blood serum and blood plasma, from the subject;
   B) analyzing said sample to determine a nutritional status of the subject as a profile vector (x);
   C) based on results of step B), calculating required nutritional supplements to improve the nutritional status of the subject in the form of a recommendation vector (d);
   D) providing at least three individualized nutritional supplements to the subject on the basis of the recommendation vector (d); and
   repeating the cycle of A)-D) after a time span of at least two days for adapting the individualized nutritional supplements provided in step D) of a second cycle based on the development of the subject at least in the time interval between the cycles,
   wherein a first cycle step C) comprises a prediction of at least one initial absorption characteristics matrix ($A_k$, $B_{p(k)}$, $C_k$, $D_{p(k)}$), and a multiplication of this at least one initial absorption characteristics matrix ($A_k$, $B_{p(k)}$, $C_k$, $D_{p(k)}$), weighted with weighting factors ($\alpha$, $\beta$, $\gamma$, $\delta$), by an initial recommendation vector ($d_1$) for a calculation of a target profile vector ($x_1^\dagger$) after a given first nutritionally supplemented time interval from the profile vector ($x_0$) as determined in step B), and
   wherein a difference between the previously calculated target profile vector ($x_n^\dagger$) and the profile vector ($x_n$) as determined in the analysis step B) is minimized by adapting and thereby personalizing at least one of the initial absorption characteristics matrix ($A_k$, $B_{p(k)}$, $D_{p(k)}$) and the weighting factors ($\alpha$, $\beta$), and using the adapted absorption characteristics matrix ($A_k$, $B_{p(k)}$, $C_k$, $D_{p(k)}$) and the weighting factors ($\alpha$, $\beta$, $\gamma$, $\delta$) for the calculation of a next required recommendation vector ($d_{n+1}$) and for the prediction of a next target profile vector ($x_{n+1}^\dagger$) after a given next nutritionally supplemented time interval,
   wherein a dimensionality of the recommendation vector (d) and the target profile vector ($x_n^\dagger$) is at least 3.

2. The method according to claim 1, wherein the at least three nutritional supplements are selected from the following group: vitamins; vitaminoids; minerals; herbals; botanicals; amino acids; enzymes carbohydrate; fiber, fatty acids; proteins; peptides; terpene-based biological molecules, including carotenoids; steroid-based biological molecules, including hormones; pyrrol-based biological molecules, including tetrapyrrols; alkaloid-based biological molecules, including caffeine; prebiotics, probiotics, flavonoids, and antioxidants.

3. The method according to claim 1, wherein step A) is taking a sample of blood, from the subject by the subject, applying the sample to a solid substrate, and immobilizing and drying the sample on said substrate to form a dried sample.

4. The method according to claim 3, wherein said solid substrate is provided with identification information.

5. The method according to claim 3, wherein said solid substrate is provided with identification information in computer readable form, including a barcode, a QR code, or an OCR-readable text.

6. The method according to claim 1, wherein for step C) individual subject related input information is taken account of.

7. The method according to claim 1, wherein for a second or further cycle further individual subject related input information of the time interval between the cycle and the corresponding actual cycle is taken account of for step C).

8. The method according to claim 1, wherein the cycles are carried out at regular intervals over an extended time span of at least 1 week, with carrying out the cycle at least every two days, and either continuing at the same frequency or reducing the frequency after having reached a steady-state situation.

9. The method according to claim 1, wherein step C) includes a step of manufacturing individualized nutritional supplements based on required nutritional supplements for the subject and step D) includes sending of these individualized nutritional supplements to the subject.

10. The method according to claim 1, wherein step B) includes a step of mass spectrometric analysis of the blood sample, further including a step of chromatographic separation or inductively coupled plasma (ICP), and determining minerals or protein markers characterizing the nutritional status of the subject based the step of mass spectrometric analysis of the blood sample, further including a step of chromatographic separation or inductively coupled plasma.

11. The method according to claim 1, wherein characteristic data specific to the subject is stored for each cycle of steps A)-D) in a database, and is used at least for the calculation in step C) and wherein the calculation in step C) includes taking account of the development of the characteristic data over time.

12. The method according to claim 1, wherein step D) further includes providing to the subject daily-recommended doses of nutrients, which are to be taken up additionally.

13. The method according to claim 1, wherein the calculation in step C) takes account of maximal or minimal recommended possible doses of the individual supplements.

14. The method according to claim 1, wherein step A) is taking a sample of blood by the subject, applying the sample to a solid substrate, provided with sample stabilization agents, and immobilizing and drying the sample on said substrate to form a dried sample, all these steps of step A) being carried out at home, and sending said sample to a place for carrying out step B).

15. The method according to claim 1, wherein step C) input information of the subject further comprises an algorithmic determination of personalized target marker values taking into account at least one of the following: sex, age, ethnic affinity, physical activity, mental activity, general status, nutritional information, climatic information, lifestyle information, molecular information, and genetic/genomic of the subject.

16. The method according to claim 1, wherein for a second or further cycle further input information of the subject of the time interval between the cycle and the corresponding actual cycle is taken account of for step C), in the form of at least one of the following information: use of the supplied nutritional advice or nutritional supplement, physical activity, mental activity, general status, general nutritional information, climatic information, lifestyle information.

17. The method according to claim 1, wherein the cycles carried out at regular intervals over an extended time span of at least 6 months, with carrying out the cycle at least every second week, or at least every month, and either continuing at the same frequency or reducing the frequency after having reached a steady-state situation.

18. The method according to claim 1, wherein the frequency of carrying out the cycles is determined by the results of the analysis in B) and the calculation in C) and wherein step D) further comprises providing information to the subject when a next sample needs to be taken.

19. The method according to claim 1, wherein step C) includes a step of manufacturing individualized nutritional supplements based on required nutritional supplements for the subject and step D) includes sending of these individualized nutritional supplements, together with instructions as to how to consume the supplements, to the subject.

20. The method according to claim 1, wherein step B) includes a step of mass spectrometric analysis of the sample taken in step A) and including a step of chromatographic separation or inductively coupled plasma (ICP), determining minerals and/or protein markers characterizing the nutritional status of the subject based the step of mass spectrometric analysis of the blood sample, further including a step of chromatographic separation or inductively coupled plasma, characterizing required needs for at least one of: vitamins, vitaminoids, minerals, herbals, botanicals, amino acids, enzymes, carbohydrate, fiber, fatty acids, proteins, peptides, terpene-based biological molecules, including carotenoids, steroid-based biological molecules, including hormones, pyrrol-based biological molecules, including tetrapyrrole, alkaloid-based biological molecules, including caffeine, prebiotics, probiotics, flavonoids, and antioxidants.

21. The method according to claim 1, wherein
characteristic data specific to the subject in the form of analysis data of the sample taken in step A) and input data of the subject,
are stored for each cycle of steps A)-D) in a database, and are used at least for the calculation in step C) and wherein the calculation in step C) includes taking account of a development of the characteristic data over time.

22. The method according to claim 1, wherein the calculation in step C) takes account of maximal or minimal recommended possible doses of the individual supplements and wherein the calculation includes calculating dose ranges for the individual supplements necessary to smoothly shift an actual nutrient profile towards an optimal range.

23. A non-transient computer-readable medium comprising a stored program, executable by a processor, including a processor of a mobile device including a smart phone, configured to perform the steps recited in claim 1.

24. A kit of parts for carrying out the method according to claim 1 comprising at least a non-transient computer-readable medium comprising a stored program executable by a processor, including a processor of a mobile device including a smart phone, configured to perform the steps recited in claim 1, a sample carrier, as well as at least one of the following items: a puncture device; a transfer device; alcohol wipes; a plaster; a gauze swab; a user manual; a specimen bag including a sachet with desiccant; an identity code, a barcode or QR code; preaddressed envelope adapted for the sample carrier.

* * * * *